(12) United States Patent
Maeda

(10) Patent No.: US 11,377,411 B2
(45) Date of Patent: Jul. 5, 2022

(54) METHOD FOR PRODUCING 3-METHYLCYCLOALKENONE COMPOUND

(71) Applicant: Takasago International Corporation, Tokyo (JP)

(72) Inventor: Hironori Maeda, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 17/278,505

(22) PCT Filed: Sep. 25, 2019

(86) PCT No.: PCT/JP2019/037435
§ 371 (c)(1),
(2) Date: Mar. 22, 2021

(87) PCT Pub. No.: WO2020/067079
PCT Pub. Date: Apr. 2, 2020

(65) Prior Publication Data
US 2022/0033336 A1    Feb. 3, 2022

(30) Foreign Application Priority Data

Sep. 25, 2018    (JP) .............................. JP2018-179516

(51) Int. Cl.
*C07C 45/62*   (2006.01)
*B01J 21/00*   (2006.01)
*B01J 21/04*   (2006.01)
*B01J 21/06*   (2006.01)
*C07C 45/74*   (2006.01)

(52) U.S. Cl.
CPC .............. *C07C 45/62* (2013.01); *B01J 21/04* (2013.01); *B01J 21/066* (2013.01); *C07C 45/74* (2013.01)

(58) Field of Classification Search
CPC .......... C07C 45/62; C07C 45/74; B01J 21/04; B01J 21/066
See application file for complete search history.

(56) References Cited

U.S. PATENT DOCUMENTS 5,081,311 A    1/1992   Huellmann et al.

FOREIGN PATENT DOCUMENTS

| CN | 108191622 A | * | 6/2018 |
| JP | 59-157047 A | | 9/1984 |
| JP | 03-081242 A | | 4/1991 |
| JP | 2018-087184 A | | 6/2018 |
| WO | WO-2010/109650 A1 | | 9/2010 |

OTHER PUBLICATIONS

Catalysis Society of Japan, "Catalyst Course vol. 5 (Engineering Edition 1) Catalyst Design," the first edition, Kodansha Ltd., Japan, Dec. 10, 1985, pp. 39-45.
Sacia et al., "Synthesis of biomass-derived methylcyclopentane as a gasoline additive via aldol condensation/hydrodeoxygenation of 2,5-hexanedione," Green Chemistry, 2015, 17:2393-2397.
Sun et al., "Vapor-phase intramolecular aldol condensation of 2,5-hexanedione to 3-methylcyclopent-2-enone over ZrO2-supported Li2O catalyst," Catalysis Communications, 2017, 92:105-108.
Tanabe et al., "Direct, practical, and powerful crossed aldol additions between ketones and ketones or aldehydes utilizing environmentally benign TiCl4-Bu3N reagent," Tetrahedron, 2002, 58:8269-8280.

* cited by examiner

*Primary Examiner* — Sikarl A Witherspoon
(74) *Attorney, Agent, or Firm* — Foley & Lardner LLP

(57) ABSTRACT

The present invention relates to a method for producing a 3-methylcycloalkenone compound and a method for producing muscone. In the presence of a zirconium oxide catalyst, a diketone represented by the following general formula (1):

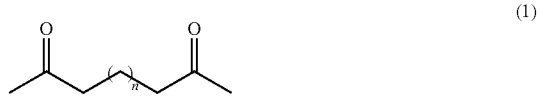

(1)

wherein in formula (1), n represents 8, 9, 10, 11 or 12, is subjected to a vapor-phase intramolecular condensation reaction, whereby a 3-methylcycloalkenone compound can be produced with high reaction efficiency. When a 3-methylcyclopentadecenone compound produced by this method is hydrogenated in a known manner, muscone can be produced efficiently.

20 Claims, 1 Drawing Sheet

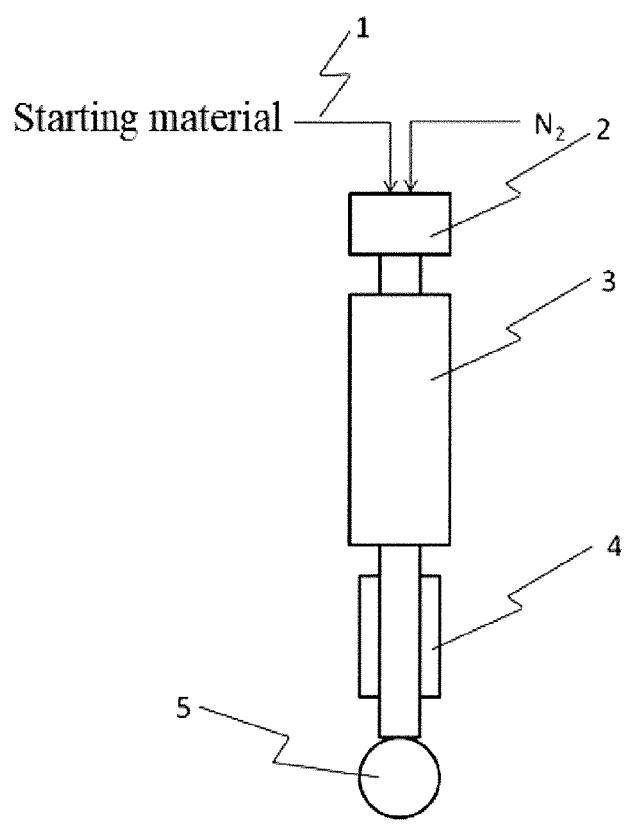

METHOD FOR PRODUCING 3-METHYLCYCLOALKENONE COMPOUND

CROSS-REFERENCE TO RELATED APPLICATIONS

This application is the U.S. National Stage of PCT/JP2019/037435, filed Sep. 25, 2019, which claims priority to JP 2018-179516, filed Sep. 25, 2018.

TECHNICAL FIELD

The present invention relates to a method for producing a 3-methylcycloalkenone compound which is a macrocyclic ketone, and particularly relates to a method for producing a 3-methylcyclopentadecenone compound which is a synthetic intermediate for muscone that is useful as a perfume. Moreover, the present invention relates to a method for producing muscone.

BACKGROUND ART

Attempts have previously been made to synthesize macrocyclic ketones. In particular, it has been known that a 3-methylcyclopentadecenone compound, which is a synthetic intermediate for muscone that is important as a perfume, is synthesized from 2,15-hexadecanedione. For example, techniques known for this purpose include intramolecular cyclization using an organozine compound (see Patent Literature 1); intramolecular cyclization using titanium tetrachloride and tributylamine and the subsequent dehydration with an acid catalyst (see Non-patent Literature 1); vapor-phase intramolecular cyclization of 2,15-hexadecanedione using any of $TiO_2$, $CeO_2$ and $ThO_2$ as a catalyst in the presence of water in an amount of 5% to 15% by mass relative to the catalyst mass (see Patent Literature 2); and vapor-phase intramolecular cyclization of 2,15-hexadecanedione using any of ZnO, CaO and MgO as a catalyst (see Patent Literature 3).

Moreover, as an example of a vapor-phase intramolecular aldol reaction using a zirconium oxide catalyst, intramolecular cyclization of 2,5-hexanedione has been known for synthesis of 3-methylcyclopentenone (see Non-patent Literature 2).

However, the above various techniques used for the production of a 3-methylcyclopentadecenone compound have some problems in terms of (i) using an equivalent or more amount of an auxiliary agent, (ii) using a special type of catalyst, (iii) requiring a high dilution system, (iv) giving a low yield, and (v) resulting in low reaction efficiency due to a low feed rate of starting material, etc.

For example, the technique shown in Patent Literature 1 is a liquid-phase reaction and therefore requires a high dilution system (i.e., the concentration of 2,15-hexadecanedione used as a starting material is about 0.2 wt/vol % in the Example section) so as to suppress intermolecular condensation, and also uses an equivalent or more amount of zinc ethyl iodide which is an expensive auxiliary agent; and hence this technique is not cost-effective.

The technique shown in Non-patent Literature 1 also requires a high dilution system (i.e., the concentration of 2,15-hexadecanedione used as a starting material is at most about 1.3 wt/vol %) and uses an equivalent or more amount of an auxiliary agent; and hence this technique is not regarded as a cost-effective production method.

The technique shown in Patent Literature 2 is designed to effect a vapor-phase reaction using any of $TiO_2$, $CeO_2$ and $ThO_2$ as a catalyst so as to suppress intermolecular condensation. However, this technique requires a special type of treatment where the catalyst is doped with an alkali metal, and the feed rate of 2,15-hexadecanedione used as a starting material relative to the catalyst is also low (i.e., the feed rate of 2,15-hexadecanedione used as a starting material is 0.01 g per hour relative to 1 g of the catalyst (LHSV=0.01) in the Example section); and hence this technique has low reaction efficiency and is not cost-effective.

The technique shown in Patent Literature 3 is designed to effect a vapor-phase reaction using any of ZnO, CaO and MgO as a catalyst. However, the feed rate of 2,15-hexadecanedione used as a starting material relative to the catalyst is low (i.e., the feed rate of 2,15-hexadecanedione used as a starting material is about 0.025 g per hour relative to 1 g of the catalyst (LHSV=0.025) in the Example section); and hence this technique has low reaction efficiency and is not regarded as a cost-effective production method.

Likewise, the technique shown in Non-patent Literature 2 is a vapor-phase intramolecular aldol condensation reaction starting from 2,5-hexanedione using a catalyst comprising zirconium oxide, and this reaction is very advantageous to an intramolecular reaction starting from a diketone containing 6 carbon atoms. For example, Non-patent Literature 3 shows an example of an intramolecular aldol condensation reaction starting from 2,5-hexanedione, and 3-methylcyclopentenone of interest can be easily obtained in high yield even in a liquid-phase reaction under low dilution conditions using inexpensive potassium phosphate as a base. Accordingly, Non-patent Literature 2 is deemed to disclose a production method completely distinct from a production method for macrocyclic ketones whose intramolecular reaction is difficult to occur.

CITATION LIST

Patent Literature

Patent Literature 1: JP S59-157047 A
Patent Literature 2: JP H03(1991)-81242 A
Patent Literature 3: WO 2010-109650

Non-Patent Literature

Non-patent Literature 1: Tetrahedron 2002, 58, 8269-8280
Non-patent Literature 2: Catalysis Communications 2017, 92, 105-108
Non-patent Literature 3: Green Chemistry 2015, 17, 2393-2397
Non-patent Literature 4: Catalysis Society of Japan, "Catalyst Course Volume 5 (Engineering Edition 1) Catalyst Design," the first edition, Kodansha Ltd., Japan, Dec. 10, 1985, pages 39-45

SUMMARY OF INVENTION

Technical Problem

There is a demand for the provision of a production method for macrocyclic ketones, which solves the problems of the above prior art techniques and achieves high reaction efficiency in a vapor-phase reaction.

Solution to Problem

As a result of extensive and intensive efforts made to solve the problems stated above, the inventors of the present invention have found that 3-methylcycloalkenone compounds of interest can be produced from corresponding diketones by vapor-phase reaction in the presence of a catalyst comprising zirconium oxide with unexpectedly high reaction efficiency. It should be noted that this finding cannot be predicted at all from the results disclosed in Comparative Example 2 of Patent Literature 3 obtained when using zirconium oxide as a catalyst (i.e., 99% conversion, 0% selectivity, 0% yield), and the experimental results obtained when using a zirconium oxide catalyst were completely unexpected. The inventors of the present invention have made further studies on the basis of these findings and have eventually completed the present invention.

Namely, the present invention is directed to [1] to [21] shown below.

[1] A method for producing a 3-methylcycloalkenone compound represented by the following general formula (2), comprising performing a vapor-phase intramolecular condensation reaction in the presence of a catalyst comprising zirconium oxide on 0.2-fold or more mass, relative to the catalyst, of a diketone represented by the following general formula (1):

[Formula 1]

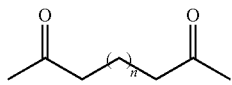

(1)

wherein in formula (1), n represents 8, 9, 10, 11 or 12,

[Formula 2]

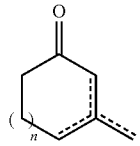

(2)

wherein in formula (2), among the three double lines each consisting of solid and dotted lines, one represents a double bond and the other two represent single bonds, the configuration of the double bond may be either cis or trans, and n is as defined in general formula (1).

[2] The method according to [1] above, wherein the catalyst is zirconium oxide alone.

[3] The method according to [1] above, wherein the catalyst further comprises an additional metal oxide other than zirconium oxide.

[4] The method according to [3] above, wherein the additional metal oxide is alumina.

[5] The method according to [4] above, wherein the content of alumina is 10% by mass or less, based on the total weight of the catalyst.

[6] The method according to any one of [1] to [5] above, wherein the diketone represented by general formula (1) is 2,15-hexadecanedione, and the 3-methylcycloalkenone compound represented by general formula (2) generated upon the intramolecular condensation reaction is a 3-methylcyclopentadecenone compound.

[7] The method according to any one of [1] to [6] above, comprising filling the catalyst into a reactor, and continuously feeding the diketone represented by general formula (1) to the reactor in an amount of 0.01 to 50 g/hr relative to 1 g of the catalyst filled into the reactor to effect the intramolecular condensation reaction.

[8] A method for producing muscone, comprising performing a vapor-phase intramolecular condensation reaction in the presence of a catalyst comprising zirconium oxide on 0.2-fold or more mass, relative to the catalyst, of 2,15-hexadecanedione to produce a 3-methylcyclopentadecenone compound represented by the following general formula (2'):

[Formula 3]

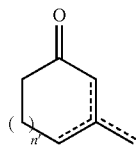

(2')

wherein among the three double lines each consisting of solid and dotted lines, one represents a double bond and the other two represent single bonds, the configuration of the double bond may be either cis or trans, and n' represents 10, and hydrogenating the resulting 3-methylcyclopentadecenone compound.

[9] The method for producing muscone according to [8] above, comprising filling the catalyst into a reactor, and continuously feeding 2,15-hexadecanedione to the reactor in an amount of 0.01 to 50 g/hr relative to 1 g of the catalyst filled into the reactor to effect the intramolecular condensation reaction.

[10] The method for producing muscone according to [8] or [9] above, wherein the catalyst is zirconium oxide alone.

[11] The method for producing muscone according to [8] or [9] above, wherein the catalyst further comprises an additional metal oxide other than zirconium oxide.

[12] The method for producing muscone according to [11] above, wherein the additional metal oxide is alumina.

[13] The method for producing muscone according to [12] above, wherein the content of alumina is 10% by mass or less, based on the total weight of the catalyst.

[14] A method for producing muscone, comprising performing the method according to [6] or [7] above to generate a 3-methylcyclopentadecenone compound-containing solution comprising a 3-methylcyclopentadecenone compound, subjecting the 3-methylcyclopentadecenone compound-containing solution to crystallization separation to remove the starting material 2,15-hexadecanedione, and hydrogenating the 2,15-hexadecanedione-free 3-methylcyclopentadecenone compound-containing solution.

[15] A method for producing muscone, comprising performing a vapor-phase intramolecular condensation reaction in the presence of a catalyst comprising zirconium oxide on 0.2-fold or more mass, relative to the catalyst, of 2,15-hexadecanedione to generate a 3-methylcyclopentadecenone compound-containing solution comprising a 3-methylcyclopentadecenone compound represented by the following general formula (2'):

[Formula 4]

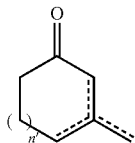

(2')

wherein among the three double lines each consisting of solid and dotted lines, one represents a double bond and the other two represent single bonds, the configuration of the double bond may be either cis or trans, and n' represents 10, and hydrogenating the 3-methylcyclopentadecenone compound contained in the 3-methylcyclopentadecenone compound-containing solution.

[16] The method for producing muscone according to [15] above, comprising subjecting the 3-methylcyclopentadecenone compound-containing solution to crystallization separation to remove the starting material 2,15-hexadecanedione, and hydrogenating the 2,15-hexadecanedione-free 3-methylcyclopentadecenone compound-containing solution.

[17] The method according to [15] or [16] above, comprising filling the catalyst into a reactor, and continuously feeding 2,15-hexadecanedione to the reactor in an amount of 0.01 to 50 g/hr relative to 1 g of the catalyst filled into the reactor to effect the intramolecular condensation reaction.

[18] The method according to any one of [15] to [17] above, wherein the catalyst is zirconium oxide alone.

[19] The method according to any one of [15] to [17] above, wherein the catalyst further comprises an additional metal oxide other than zirconium oxide.

[20] The method according to [19] above, wherein the additional metal oxide is alumina.

[21] The method according to [20] above, wherein the content of alumina is 10% by mass or less, based on the total weight of the catalyst.

Moreover, the present invention is directed to [1] to [7] shown below.

[1] A method for producing a 3-methylcycloalkenone compound represented by the following general formula (2), which is characterized by performing a vapor-phase intramolecular condensation reaction in the presence of a zirconium oxide catalyst on a diketone represented by the following general formula (1):

[Formula 5]

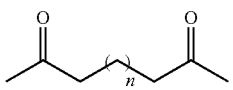

(1)

wherein in formula (1), n represents 8, 9, 10, 11 or 12,

[Formula 6]

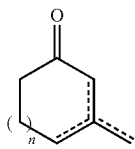

(2)

wherein in formula (2), among the three double lines each consisting of solid and dotted lines, one represents a double bond and the other two represent single bonds, the double bond may be in either cis or trans configuration, and n is as defined in general formula (1).

[2] The method according to [1] above, characterized by performing the vapor-phase intramolecular condensation reaction in the presence of a zirconium oxide catalyst comprising a metal oxide on the diketone represented by general formula (1) to produce the 3-methylcycloalkenone compound represented by general formula (2).

[3] The method according to [2] above, characterized in that the additional metal oxide is alumina.

[4] The method according to [3] above, characterized in that the content of alumina is 10% by mass or less, based on the total weight of the catalyst.

[5] The method according to any one of [1] to [4] above, characterized in that the diketone represented by general formula (1) is 2,15-hexadecanedione, and the 3-methylcycloalkenone compound represented by general formula (2) generated upon the intramolecular condensation reaction is a 3-methylcyclopentadecenone compound.

[6] The method according to any one of [1] to [5] above, characterized by filling the catalyst into a reactor, and continuously feeding the diketone represented by general formula (1) to the reactor in an amount of 0.01 to 50 g/hr relative to 1 g of the catalyst filled into the reactor to effect the intramolecular condensation reaction.

[7] A method for producing muscone, which is characterized by performing the method according to [5] or [6] above to generate a 3-methylcyclopentadecenone compound-containing solution, subjecting the 3-methylcyclopentadecenone compound-containing solution to crystallization separation to remove the starting material 2,15-hexadecanedione, and hydrogenating the 2,15-hexadecanedione-free 3-methylcyclopentadecenone compound-containing solution.

Advantageous Effects of Invention

The production method of the present invention enables the production of 3-methylcycloalkenone compounds from corresponding diketones with higher reaction efficiency than that of conventional production methods. Further, in a preferred embodiment, the present invention enables the production of 3-methylcycloalkenone compounds from corresponding diketones with high conversion and high selectivity while maintaining a high feed rate of the starting materials.

BRIEF DESCRIPTION OF DRAWINGS

FIG. 1 schematically illustrates an embodiment of a production apparatus which may be effectively used in the method of the present invention for producing a 3-methylcycloalkenone compound.

DESCRIPTION OF EMBODIMENTS

The present invention will be described in more detail below.

The present invention is directed to a method for producing a 3-methylcycloalkenone compound represented by the following general formula (2), comprising performing a vapor-phase intramolecular condensation reaction in the presence of a catalyst comprising zirconium oxide on 0.2-fold or more mass, relative to the catalyst, of a diketone represented by the following general formula (1):

[Formula 7]

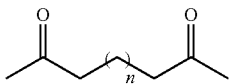

(1)

wherein in formula (1), n represents 8, 9, 10, 11 or 12,

[Formula 8]

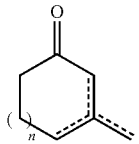

(2)

wherein in formula (2), among the three double lines each consisting of solid and dotted lines, one represents a double bond and the other two represent single bonds, the configuration of the double bond may be either cis or trans, and n is as defined in general formula (1).

<Starting Material Compound>

A diketone used as a starting material compound in the present invention is represented by the following general formula (1):

[Formula 9]

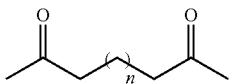

(1)

wherein in formula (1), n represents 8, 9, 10, 11 or 12.

The diketone used as a starting material compound in the present invention is specifically exemplified by 2,13-tetradecanedione, 2,14-pentadecanedione, 2,15-hexadecanedione, 2,16-heptadecanedione and 2,17-octadecanedione. In the present invention, these diketones may be used either alone or in combination.

Such a starting material diketone may be produced in any manner. For example, it is possible to use a diketone produced by reacting an aliphatic halide with ketones in the presence of a base.

It should be noted that when 2,15-hexadecanedione is used as a starting material diketone in the present invention, a 3-methylcyclopentadecenone compound obtained therefrom upon intramolecular condensation reaction may be hydrogenated to thereby obtain muscone that is useful as a perfume.

The amount of the diketone used as a starting material compound in the present invention is 0.2-fold or more mass, preferably 0.3-fold or more mass, more preferably 1-fold or more mass, relative to the catalyst. When the diketone is used in an amount of 0.2-fold or more mass relative to the catalyst, the desired 3-methylcycloalkenone compound can be produced with high reaction efficiency. Moreover, the desired 3-methylcycloalkenone compound can be produced with high conversion and high selectivity while maintaining a high feed rate of the starting material. In terms of maintaining high conversion, the amount of the diketone to be used is, but not limited to, preferably 1000-fold or less mass, more preferably 500-fold or less mass, relative to the catalyst.

<Catalyst>

The catalyst used in the present invention may be of single component consisting of zirconium oxide (zirconium dioxide ($ZrO_2$), also referred to as zirconia) or may comprise zirconium oxide and one or more additional components. When the catalyst comprises zirconium oxide and one or more additional components, the catalyst may be a physical mixture of zirconium oxide and an additional component(s), or zirconium oxide and an additional component(s) may form a composite. When zirconium oxide and an additional component(s) form a composite, the morphology of the composite is not limited in any way. For example, zirconium oxide and an additional component(s) may form a composite at the atomic level, or an additional component(s) may be supported, e.g., on the surface of zirconium oxide to form a composite. Such a composite of zirconium oxide and an additional component(s) may be produced in any manner, for example, by impregnation, kneading or coprecipitation techniques as appear in Non-patent Literature 4.

Examples of additional components include, but are not limited to, $SO_4$, $PO_4$, $B_2O_3$ and metal oxides (except for zirconium oxide), etc. Specific examples of metal oxides include $Al_2O_3$ (alumina), $SiO_2$, $WO_3$, CaO, MgO, BeO, $Na_2O$, $K_2O$, $Li_2O$, $Cs_2O$, $TiO_2$, $CeO_2$, $VO_2$, $V_2O_5$, $Cr_2O_3$, MnO, $MnO_2$, $Mn_2O_3$, $Fe_2O_3$, $Co_3O_4$, NiO, CuO, $Ga_2O_3$, $GeO_2$, $Rb_2O$, SrO, $Y_2O_3$, $Nb_2O_5$, $In_2O_3$, $SnO_2$, $MoO_3$, $Sb_2O_5$, $ThO_2$, CdO, ZnO, BaO, $Ta_2O_5$, $Bi_2O_3$, $La_2O_3$, $Pr_2O_3$, $Nd_2O_3$, $Sm_2O_3$, $Eu_2O_3$, $Gd_2O_3$, $Tb_2O_3$, $Dy_2O_3$, $Ho_2O_3$, $Tm_2O_3$, $Yb_2O_3$, and $Lu_2O_3$, etc. Among them, $Al_2O_3$ is preferred in terms of reactivity and stability.

The amount of such a metal oxide(s) contained in the catalyst is not limited in any way, but it is preferably 10% by mass or less, more preferably 5% by mass or less, particularly preferably 3% by mass or less, based on the total weight of the catalyst.

Zirconium oxide for use as a catalyst or a catalyst comprising zirconium oxide may be used in the uncalcined state or may be subjected to calcination treatment before use. The temperature for calcination treatment of the catalyst is preferably 400° C. to 1000° C., more preferably 600° C. to 900° C., and particularly preferably 700° C. to 900° C. Likewise, the calcination time is preferably 1 to 48 hours, more preferably 2 to 36 hours, and particularly preferably 3 to 12 hours.

The crystal structure of zirconium oxide for use as a catalyst or a catalyst comprising zirconium oxide is not limited in any way, and it is possible to use any structure of monoclinic, tetragonal, cubic or amorphous system.

Zirconium oxide for use as a catalyst or a catalyst comprising zirconium oxide may be used in either powder or molded form, but is preferably used in molded from in terms of its handling. The molded form may be of any size and any shape. For example, it is possible to use the catalyst in molded form of pellet (i.e., short columnar), spherical, cubic, rectangular, discal, ellipsoidal or cylindrical shape having a size of 1 to 10 mm, preferably around 1 to 5 mm.

The BET specific surface area of zirconium oxide for use as a catalyst or a catalyst comprising zirconium oxide is not limited in any way, but it is preferably 10 $m^2$/g to 200 $m^2$/g, and more preferably 10 $m^2$/g to 100 $m^2$/g. It should be noted that the specific surface area tends to be smaller at a higher calcination temperature in most cases.

<Reactor>

Any type of reactor may be used, as long as it is a reaction apparatus in which the starting material diketone can be vaporized and contacted to the catalyst to effect an intramolecular condensation reaction.

Above all, a catalyst packed bed reactor is preferred for use as a reactor. A catalyst packed bed reactor is designed such that a catalyst is filled in layered form into a cylindrical container, into one end of which a starting material is fed and from the other end of which a reaction product is discharged. FIG. 1 schematically illustrates an embodiment of a catalyst packed bed reactor. The starting material may be fed into starting material feeding line 1, vaporized in vaporizer 2 (equipped with a heater), continuously fed into one end of catalyst packed reactor 3 (equipped with a heater), and contacted with the catalyst in the vapor phase state to cause a reaction. The product may be continuously discharged from the other end of catalyst packed reactor 3 (equipped with a heater), cooled with condenser 4, and collected into reaction product receiver 5. In the present invention, such a catalyst packed bed reactor may have any inner diameter and any length, and may be designed to have a size suitable for each situation.

When the present invention is carried out using a catalyst packed bed reactor, it is preferred, but not limited to, that zirconium oxide for use as a catalyst or a catalyst comprising zirconium oxide is filled in layered form into a cylindrical reactor, into which the starting material diketone vaporized with a vaporizer or the like is continuously fed through one end of the catalyst packed bed reactor, and contacted in the vapor phase state with the zirconium oxide for use as a catalyst or the catalyst comprising zirconium oxide to cause an intramolecular condensation reaction, while a product comprising a 3-methylcycloalkenone compound is continuously discharged from the other end of the catalyst packed bed reactor.

<Solvent>

The starting material diketone may be used directly or may be dissolved in a solvent before use. As a solvent, a hydrocarbon is generally used and, in particular, an aliphatic hydrocarbon containing 6 to 14 carbon atoms is preferred, but any solvent may be used as long as it is inert to the intended reaction. Specific examples include toluene, xylene, mesitylene, decane, dodecane, isododecane, decalin, and tetradecane, etc.

The amount of such a solvent to be used is not limited in any way, but it is 0- to 100-fold mass, preferably 5- to 50-fold mass, particularly preferably 5- to 30-fold mass, relative to the starting material diketone.

<Carrier Gas>

A carrier gas is not limited in any way, as long as it is inert to the intended reaction. For example, nitrogen or carbon dioxide may be used for this purpose. The amount of such a carrier gas to be used is generally 0.2 L to 20 L relative to 1 g of the starting material, because too high an amount is not cost-effective while too low an amount is of no help in controlling side reactions.

<Evaporation Unit Temperature>

The temperature of a vaporizer where the starting material diketone is vaporized, i.e., the temperature of an evaporation unit is generally 250° C. to 500° C., but it is not limited to this range and may be a temperature at which the starting material diketone is completely vaporized.

<Feed Rate of Starting Material>

When the starting material diketone is continuously fed to the reactor to effect an intramolecular condensation reaction, the feed rate of the starting material diketone to the reactor may be adjusted as appropriate depending on the type of the starting material diketone, the type and structure of the reactor, etc. For example, the starting material diketone may be continuously fed to the reactor in an amount of 0.01 to 50 g/hr, preferably 0.05 to 20 g/hr, particularly preferably 0.05 to 5 g/hr, relative to 1 g of the catalyst filled into the reactor, to effect an intramolecular condensation reaction with high reaction efficiency. The production method of the present invention allows intramolecular condensation with high reaction efficiency even when increasing the feed rate of the starting material as mentioned above. Further, in a preferred embodiment, the present invention enables the production of a 3-methylcycloalkenone compound with high conversion and high selectivity and with high reaction efficiency even when increasing the feed rate of the starting material.

<Reaction Temperature>

The reaction temperature is preferably in the range of 250° C. to 500° C., and particularly preferably in the range of 300° C. to 450° C., because the reaction does not proceed at too low a temperature while side reactions will proceed at too high a temperature.

<Product Collection>

The reaction product may be collected by being cooled to between 0° C. and 60° C. This reaction product (hereinafter referred to as a reaction product solution) is mainly composed of the solvent used, the 3-methylcycloalkenone compound generated, and the starting material diketone remaining unreacted. From the resulting reaction product solution, the 3-methylcycloalkenone compound and the starting material diketone remaining unreacted can be separated individually by any known separation techniques such as crystallization separation or distillation.

The unreacted diketone collected by known separation techniques such as crystallization separation or distillation from the resulting reaction product solution may be recycled.

The thus obtained 3-methylcycloalkenone compound is represented by the following general formula (2):

[Formula 10]

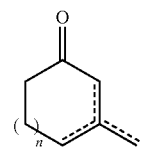

(2)

wherein in formula (2), among the three double lines each consisting of solid and dotted lines, one represents a double bond and the other two represent single bonds, the configuration of the double bond may be either cis or trans, and n is as defined in general formula (1). In more detail, it is (E)-3-methyl-2-cycloalkenone, (Z)-3-methyl-2-cycloalkenone, (E)-3-methyl-3-cycloalkenone, (Z)-3-methyl-3-cycloalkenone, or 3-methylene-cycloalkanone.

<Method for Producing Muscone>

When 2,15-hexadecanedione is used as a starting material diketone, the reaction product is mainly composed of a 3-methylcyclopentadecenone compound-containing solution comprising the solvent used, the 3-methylcyclopentadecenone compound generated, and 2,15-hexadecanedione remaining unreacted. After removal of the unreacted 2,15-hexadecanedione by crystallization or distillation from the 3-methylcyclopentadecenone compound-containing solution obtained as the reaction product solution, the 3-methylcyclopentadecenone compound may be used directly, i.e., in the form of the 3-methylcyclopentadecenone compound-containing solution comprising the solvent used, or the 3-methylcyclopentadecenone compound-containing solution may further be treated to replace the solvent used with an appropriate solvent, followed by hydrogenation of the olefin moiety in a known manner to give muscone. Alternatively, the 3-methylcyclopentadecenone compound-containing solution obtained as the reaction product solution may be used directly, i.e., in the form of the 3-methylcyclopentadecenone compound-containing solution comprising the solvent used and 2,15-hexadecanedione remaining unreacted. or the 3-methylcyclopentadecenone compound-containing solution may be treated to replace the solvent used with an appropriate solvent, followed by hydrogenation of the olefin moiety in a known manner to give muscone.

The olefin moiety of the 3-methylcyclopentadecenone compound may be hydrogenated in any manner. For example, the olefin moiety may be hydrogenated in the presence of a palladium catalyst, as described in Patent Literature 2, or the olefin moiety may be hydrogenated in the presence of a ruthenium catalyst, as described in Patent Literature 3.

Namely, the present invention also encompasses a method for producing muscone, comprising performing a vapor-phase intramolecular condensation reaction in the presence of a catalyst comprising zirconium oxide on 0.2-fold or more mass, relative to the catalyst, of 2,15-hexadecanedione to generate a 3-methylcyclopentadecenone compound represented by the following general formula (2'):

[Formula 11]

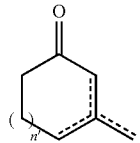

(2')

wherein among the three double lines each consisting of solid and dotted lines, one represents a double bond and the other two represent single bonds, the configuration of the double bond may be either cis or trans, and n' represents 10, and hydrogenating the 3-methylcyclopentadecenone compound.

Moreover, the present invention also encompasses a method for producing muscone, comprising performing a vapor-phase intramolecular condensation reaction in the presence of a catalyst comprising zirconium oxide on 0.2-fold or more mass, relative to the catalyst, of 2,15-hexadecanedione to generate a 3-methylcyclopentadecenone compound-containing solution comprising a 3-methylcyclopentadecenone compound represented by the following general formula (2'):

[Formula 12]

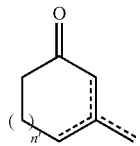

(2')

wherein among the three double lines each consisting of solid and dotted lines, one represents a double bond and the other two represent single bonds, the configuration of the double bond may be either cis or trans, and n' represents 10, and hydrogenating the 3-methylcyclopentadecenone compound contained in the 3-methylcyclopentadecenone compound-containing solution.

Moreover, the present invention also encompasses a method for producing muscone, comprising performing a vapor-phase intramolecular condensation reaction in the presence of a catalyst comprising zirconium oxide on 0.2-fold or more mass, relative to the catalyst, of 2,15-hexadecanedione to generate a 3-methylcyclopentadecenone compound-containing solution comprising a 3-methylcyclopentadecenone compound represented by the following general formula (2'):

[Formula 13]

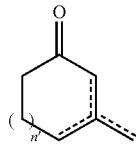

(2')

wherein among the three double lines each consisting of solid and dotted lines, one represents a double bond and the other two represent single bonds, the configuration of the double bond may be either cis or trans, and n' represents 10, subjecting the 3-methylcyclopentadecenone compound-containing solution to crystallization separation to remove the starting material 2,15-hexadecanedione, and hydrogenating the 2,15-hexadecanedione-free 3-methylcyclopentadecenone compound-containing solution.

EXAMPLES

The present invention will be further described in more detail by way of the following examples and comparative examples, which are not intended to limit the present invention.

In the following examples and comparative examples, the reaction products were measured by gas chromatography (GLC).

Analytical instrument used: GC2010 gas chromatograph (Shimadzu Corporation, Japan)

Column: Agilent BC-WAX (0.25 mm×30 m×0.3 μm)

Detector: FID

Moreover, in the following examples, conversion, selectivity and yield were determined according to the following equations.

Conversion (%)=$\{(W_0-W_1)/W_0\}\times 100$

Selectivity (%)=$\{W_d/(W_0-W_1)\}\times 100$

Yield (%) $\{W_d/W_0\}\times 100$

It should be noted that $W_0$, $W_1$ and $W_a$ in the above equations are as defined below.

$W_0$=the number of moles of the starting material (the total number of moles of the starting material fed to the reactor)

$W_1$=the remaining number of moles of the starting material (the number of moles of the starting material remaining in the reaction product)

$W_a$=the number of moles of the desired product (i.e., a corresponding 3-methylcycloalkenone compound) in the reaction product

Example 1

Into the bottom of a catalyst packed bed reactor (21.5 mmϕ, 700 mm long), 70 g of magnetic Raschig rings (TO-TOKU Engineering Corporation, Japan) was filled, onto which 100 g of uncalcined zirconium oxide pellets (Daiichi Kigenso Kagaku Kogyo Co., Ltd., Japan) (5 mmϕ, BET specific surface area: 63.6 m²/g) was then filled as a catalyst, onto which 70 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 0.2-fold mass relative to the catalyst. The collected reaction product solution was analyzed by gas chromatography to determine conversion, 3-methylcyclopentadecenone compound selectivity and yield. The results obtained are shown in Table 1 described later.

Example 2

Into the bottom of a catalyst packed bed reactor (21.5 mmϕ, 700 mm long), 70 g of magnetic Raschig rings (TO-TOKU Engineering Corporation, Japan) was filled, onto which 100 g of uncalcined zirconium oxide pellets (Daiichi Kigenso Kagaku Kogyo Co., Ltd., Japan) (5 mmϕ, BET specific surface area: 63.6 m²/g) was then filled as a catalyst, onto which 70 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 100 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 3

Into the bottom of a catalyst packed bed reactor (21.5 mmϕ, 700 mm long), 85 g of magnetic Raschig rings (TO-TOKU Engineering Corporation, Japan) was filled, onto which 20 g of uncalcined zirconium oxide pellets (Daiichi Kigenso Kagaku Kogyo Co., Ltd., Japan) (5 mmϕ, BET specific surface area: 63.6 m²/g) was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 4

Into the bottom of a catalyst packed bed reactor (21.5 mmϕ, 700 mm long), 85 g of magnetic Raschig rings (TO-TOKU Engineering Corporation, Japan) was filled, onto which 20 g of uncalcined zirconium oxide pellets (Daiichi Kigenso Kagaku Kogyo Co., Ltd., Japan) (5 mmϕ, BET specific surface area: 63.6 m²/g) was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 6 hours. The 2,15-hexadecanedione was used in an amount of 0.3-fold mass relative to the catalyst. The collected reaction product solution was analyzed by gas chromatography to determine conversion, 3-methylcyclopentadecenone compound selectivity and yield. The results obtained are shown in Table 1 described later.

Example 5

Into the bottom of a catalyst packed bed reactor (21.5 mmϕ, 700 mm long), 85 g of magnetic Raschig rings (TO-TOKU Engineering Corporation, Japan) was filled, onto which 20 g of uncalcined zirconium oxide pellets (Daiichi Kigenso Kagaku Kogyo Co., Ltd., Japan) (5 mmϕ, BET specific surface area: 63.6 m²/g) was then filled as a catalyst, onto which 85 g of the magnetic Raschig rings was further filled. A vaporizer was equipped on the top of the catalyst packed bed reactor, and the vaporizer was heated to 300° C. and the catalyst packed bed reactor was heated to 300° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 6

Into the bottom of a catalyst packed bed reactor (21.5 mmϕ, 700 mm long), 85 g of magnetic Raschig rings (TO-TOKU Engineering Corporation, Japan) was filled, onto which 20 g of calcined zirconium oxide pellets obtained by calcining zirconium oxide pellets (Daiichi Kigenso Kagaku Kogyo Co., Ltd., Japan) (5 mmϕ, BET specific surface area 63.6 m$^2$/g) in air at 700° C. for 3 hours was then filled as a catalyst, onto which 85 g of the magnetic Raschig rings was further filled. A vaporizer was equipped on the top of the catalyst packed bed reactor, and the vaporizer was heated to 300° C. and the catalyst packed bed reactor was heated to 300° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 7

Into the bottom of a catalyst packed bed reactor (21.5 mmϕ, 700 mm long), 85 g of magnetic Raschig rings (TO-TOKU Engineering Corporation, Japan) was filled, onto which 20 g of calcined zirconium oxide pellets obtained by calcining zirconium oxide pellets (Daiichi Kigenso Kagaku Kogyo Co., Ltd., Japan) (5 mmϕ, BET specific surface area: 63.6 m$^2$/g) in air at 900° C. for 3 hours was then filled as a catalyst, onto which 85 g of the magnetic Raschig rings was further filled. A vaporizer was equipped on the top of the catalyst packed bed reactor, and the vaporizer was heated to 300° C. and the catalyst packed bed reactor was heated to 300° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 8

Into the bottom of a catalyst packed bed reactor (21.5 mmϕ, 700 mm long), 85 g of magnetic Raschig rings (TO-TOKU Engineering Corporation, Japan) was filled, onto which 20 g of calcined composite zirconium oxide pellets containing 0.24% by mass of alumina obtained by calcining composite zirconium oxide pellets containing 0.24% by mass of alumina (Daiichi Kigenso Kagaku Kogyo Co., Ltd., Japan) (5 mmϕ, BET specific surface area: 80.5 m$^2$/g) in air at 550° C. for 3 hours was then filled as a catalyst, onto which 85 g of the magnetic Raschig rings was further filled. A vaporizer was equipped on the top of the catalyst packed bed reactor, and the vaporizer was heated to 300° C. and the catalyst packed bed reactor was heated to 300° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 9

Into the bottom of a catalyst packed bed reactor (21.5 mmϕ, 700 mm long), 85 g of magnetic Raschig rings (TO-TOKU Engineering Corporation, Japan) was filled, onto which 20 g of calcined composite zirconium oxide pellets containing 0.24% by mass of alumina obtained by calcining composite zirconium oxide pellets containing 0.24% by mass of alumina (Daiichi Kigenso Kagaku Kogyo Co., Ltd., Japan) (5 mmϕ, BET specific surface area: 80.5 m$^2$/g) in air at 800° C. for 3 hours was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 10

Into the bottom of a catalyst packed bed reactor (21.5 mmϕ, 700 mm long), 85 g of magnetic Raschig rings (TO-TOKU Engineering Corporation, Japan) was filled, onto which 20 g of calcined composite zirconium oxide pellets containing 0.70% by mass of alumina obtained by calcining composite zirconium oxide pellets containing 0.70% by mass of alumina (Daiichi Kigenso Kagaku Kogyo Co., Ltd., Japan) (5 mmϕ, BET specific surface area: 89.3 m²/g) in air at 550° C. for 3 hours was then filled as a catalyst, onto which 85 g of the magnetic Raschig rings was further filled.

A vaporizer was equipped on the top of the catalyst packed bed reactor, and the vaporizer was heated to 300° C. and the catalyst packed bed reactor was heated to 300° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 11

Into the bottom of a catalyst packed bed reactor (21.5 mmϕ, 700 mm long), 85 g of magnetic Raschig rings (TO-TOKU Engineering Corporation, Japan) was filled, onto which 20 g of calcined composite zirconium oxide pellets containing 0.74% by mass of alumina (Daiichi Kigenso Kagaku Kogyo Co., Ltd., Japan) (5 mmϕ, BET specific surface area: 27.4 m²/g) which had been calcined in air at 800° C. for 3 hours was then filled as a catalyst, onto which 85 g of the magnetic Raschig rings was further filled.

A vaporizer was equipped on the top of the catalyst packed bed reactor, and the vaporizer was heated to 340° C. and the catalyst packed bed reactor was heated to 340° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 1.0-fold mass relative to the catalyst. The collected reaction product solution was analyzed by gas chromatography to determine conversion, 3-methylcyclopentadecenone compound selectivity and yield. The results obtained are shown in Table 1 described later.

Example 12

Into the bottom of a catalyst packed bed reactor (21.5 mmϕ, 700 mm long), 85 g of magnetic Raschig rings (TO-TOKU Engineering Corporation, Japan) was filled, onto which 10 g of calcined composite zirconium oxide pellets containing 0.74% by mass of alumina (Daiichi Kigenso Kagaku Kogyo Co., Ltd., Japan) (5 mmϕ, BET specific surface area: 27.4 m²/g) which had been calcined in air at 800° C. for 3 hours was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 2.0-fold mass relative to the catalyst. The collected reaction product solution was analyzed by gas chromatography to determine conversion, 3-methylcyclopentadecenone compound selectivity and yield. The results obtained are shown in Table 1 described later.

Example 13

Into the bottom of a catalyst packed bed reactor (21.5 mmϕ, 700 mm long), 85 g of magnetic Raschig rings (TO-TOKU Engineering Corporation, Japan) was filled, onto which 10 g of calcined composite zirconium oxide pellets containing 1.01% by mass of alumina obtained by calcining composite zirconium oxide pellets containing 1.01% by mass of alumina (Daiichi Kigenso Kagaku Kogyo Co., Ltd., Japan) (5 mmϕ, BET specific surface area: 106 m²/g) in air at 800° C. for 3 hours was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 2.0-fold mass relative to the catalyst. The collected reaction product solution was analyzed by gas chromatography to determine conversion, 3-methylcyclopentadecenone compound selectivity and yield. The results obtained are shown in Table 1 described later.

Example 14

Into the bottom of a catalyst packed bed reactor (21.5 mmϕ, 700 mm long), 85 g of magnetic Raschig rings (TO-TOKU Engineering Corporation, Japan) was filled, onto which 10 g of calcined composite zirconium oxide pellets containing 2.98% by mass of alumina obtained by calcining composite zirconium oxide pellets containing 2.98% by mass of alumina (Daiichi Kigenso Kagaku Kogyo Co., Ltd., Japan) (5 mmϕ, BET specific surface area: 182 m²/g) in air at 800° C. for 3 hours was then filled as a catalyst, onto which 85 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 30 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 2.0-fold mass relative to the catalyst. The collected reaction product solution was analyzed by gas chromatography to determine conversion, 3-methylcyclopentadecenone compound selectivity and yield. The results obtained are shown in Table 1 described later.

Example 15

Into the bottom of a catalyst packed bed reactor (21.5 mm+, 700 mm long), 85 g of magnetic Raschig rings (TO-TOKU Engineering Corporation, Japan) was filled, onto which 10 g of calcined composite zirconium oxide pellets containing 0.76% by mass of alumina (Daiichi Kigenso Kagaku Kogyo Co., Ltd., Japan) (2 mm+, BET specific surface area: 31.1 m²/g) which had been calcined in air at 800° C. for 3 hours was then filled as a catalyst, onto which 85 g of the magnetic Raschig rings was further filled. A vaporizer was equipped on the top of the catalyst packed bed reactor, and the vaporizer was heated to 400° C. and the catalyst packed bed reactor was heated to 380° C. While passing nitrogen as a carrier gas at a rate of 12 L/hr, a solution containing 3.65% by mass of 2,15-hexadecanedione in xylene was introduced at a rate of 77 g/hr through the vaporizer into the catalyst packed bed reactor to effect an intramolecular condensation reaction. This reaction product was cooled to 10° C. or below and collected.

This reaction was continued for 20 hours. The 2,15-hexadecanedione was used in an amount of 5.6-fold mass relative to the catalyst. The collected reaction product solution was analyzed by gas chromatography to determine conversion, 3-methylcyclopentadecenone compound selectivity and yield. The results obtained are shown in Table 1 described later.

Example 16

Into the bottom of a catalyst packed bed reactor (21.5 mmφ, 700 mm long), 85 g of magnetic Raschig rings (TO-TOKU Engineering Corporation, Japan) was filled, onto which 20 g of calcined composite zirconium oxide pellets containing 0.76% by mass of alumina (Daiichi Kigenso Kagaku Kogyo Co., Ltd., Japan) (2 mmφ, BET specific surface area: 31.1 m²/g) which had been calcined in air at 800° C. for 3 hours was then filled as a catalyst, onto which 85 g of the magnetic Raschig rings was further filled. A vaporizer was equipped on the top of the catalyst packed bed reactor, and the vaporizer was heated to 410° C. and the catalyst packed bed reactor was heated to 392° C. While passing nitrogen as a carrier gas at a rate of 24 L/hr, a solution containing 7.04% by mass of 2,15-hexadecanedione in xylene was introduced at a rate of 142 g/hr through the vaporizer into the catalyst packed bed reactor to effect an intramolecular condensation reaction. This reaction product was cooled to 10° C. or below and collected.

This reaction was continued for 100 hours. The 2,15-hexadecanedione was used in an amount of 50.0-fold mass relative to the catalyst. The collected reaction product solution was analyzed by gas chromatography to determine conversion, 3-methylcyclopentadecenone compound selectivity and yield. The results obtained are shown in Table 1 described later.

TABLE 1

| | Catalyst comprising zirconium oxide | | | Intramolecular condensation reaction of diketone | | | Mass ratio of diketone | Reaction product | | |
|---|---|---|---|---|---|---|---|---|---|---|
| | Alumina content (% by mass) | Calcination temperature (° C.) | BET specific surface area[1] (m²/g) | Feed rate of starting material[2] | Condensation temperature (° C.) | Reaction time (hour) | relative to catalyst (fold mass) | Conversion (%) | Selectivity (%) | Yield (%) |
| Example 1 | 0.0 | — | 63.6 | 0.01 | 340 | 20 | 0.2 | 99 | 4 | 4 |
| Example 2 | 0.0 | — | 63.6 | 0.01 | 340 | 100 | 1.0 | 91 | 45 | 41 |
| Example 3 | 0.0 | — | 63.6 | 0.05 | 340 | 20 | 1.0 | 60 | 63 | 37 |
| Example 4 | 0.0 | — | 63.6 | 0.05 | 340 | 6 | 0.3 | 81 | 42 | 34 |
| Example 5 | 0.0 | — | 63.6 | 0.05 | 300 | 20 | 1.0 | 43 | 51 | 22 |
| Example 6 | 0.0 | 700 | — | 0.05 | 300 | 20 | 1.0 | 63 | 57 | 36 |
| Example 7 | 0.0 | 900 | — | 0.05 | 300 | 20 | 1.0 | 40 | 82 | 33 |
| Example 8 | 0.24 | 550 | — | 0.05 | 300 | 20 | 1.0 | 80 | 46 | 37 |
| Example 9 | 0.24 | 800 | — | 0.05 | 340 | 20 | 1.0 | 73 | 74 | 54 |
| Example 10 | 0.70 | 550 | — | 0.05 | 300 | 20 | 1.0 | 88 | 44 | 39 |
| Example 11 | 0.74 | 800 | 27.4 | 0.05 | 340 | 20 | 1.0 | 95 | 65 | 62 |
| Example 12 | 0.74 | 800 | 27.4 | 0.10 | 340 | 20 | 2.0 | 77 | 72 | 55 |
| Example 13 | 1.01 | 800 | — | 0.10 | 340 | 20 | 2.0 | 75 | 71 | 53 |
| Example 14 | 2.98 | 800 | — | 0.10 | 340 | 20 | 2.0 | 72 | 66 | 48 |
| Example 15 | 0.76 | 800 | 31.1 | 0.28 | 380 | 20 | 5.6 | 91 | 75 | 68 |
| Example 16 | 0.76 | 800 | 31.1 | 0.50 | 392 | 100 | 50.0 | 88 | 78 | 69 |

[1] "—" means not measured
[2] Feed rate (g) of the starting material per hour relative to 1 g of the catalyst (unit: g/g-cat · hr)

Comparative Example 1

Into the bottom of a catalyst packed bed reactor (21.5 mmφ, 700 mm long), 70 g of magnetic Raschig rings (TO-TOKU Engineering Corporation, Japan) was filled, onto which 100 g of uncalcined zirconium oxide pellets (Daiichi Kigenso Kagaku Kogyo Co., Ltd., Japan) (5 mmφ, BET specific surface area: 63.6 m²/g) was then filled as a catalyst, onto which 70 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 6 hours. The 2,15-hexadecanedione was used in an amount of 0.06-fold mass relative to the catalyst. The collected reaction product solution was analyzed by gas chromatography to determine conversion, 3-methylcyclopentadecenone compound selectivity and yield. The results obtained are shown in Table 2 described later.

Comparative Example 2

Into the bottom of a catalyst packed bed reactor (21.5 mmφ, 700 mm long), 70 g of magnetic Raschig rings (TO-TOKU Engineering Corporation, Japan) was filled, onto which 100 g of uncalcined zirconium oxide pellets (Daiichi Kigenso Kagaku Kogyo Co., Ltd., Japan) (5 mmφ, BET specific surface area: 63.6 m²/g) was then filled as a catalyst, onto which 70 g of the magnetic Raschig rings was further filled. A vaporizer was equipped on the top of the catalyst packed bed reactor, and the vaporizer was heated to 340° C. and the catalyst packed bed reactor was heated to 340° C. While passing nitrogen as a carrier gas at a rate of 12 L/hr, a solution containing 3.65% by mass of 2,15-hexadecanedione in xylene was introduced at a rate of 27 g/hr through the vaporizer into the catalyst packed bed reactor to effect an intramolecular condensation reaction. This reaction product was cooled to 10° C. or below and collected.

This reaction was continued for 12 hours. The 2,15-hexadecanedione was used in an amount of 0.12-fold mass relative to the catalyst. The collected reaction product solution was analyzed by gas chromatography to determine conversion, 3-methylcyclopentadecenone compound selectivity and yield. The results obtained are shown in Table 2 described later.

3-methylcyclopentadecenone compound and was free from 2,15-hexadecanedione. The dry weight of the resulting crystal was 132 g, and the content of 2,15-hexadecanedione was 123 g.

The thus obtained heptane solution containing the 3-methylcyclopentadecenone compound was taken in an amount of 138 g and concentrated, followed by addition of 5% by mass of palladium on carbon (0.1 g) as a catalyst and 2-propanol (80 g) as a solvent to effect a reaction under 2.0 MPa hydrogen pressure at 25° C. for 20 hours. After the reaction, 5% by mass of palladium on carbon as a catalyst was removed by filtration separation, and the filtrate was concentrated and rectified to obtain 40 g of muscone with a purity of 99% by mass.

INDUSTRIAL APPLICABILITY

The present invention provides efficient production methods for muscone which is useful as a perfume, 3-methylcyclopentadecenone which is a synthetic intermediate for muscone, and other 3-methylcycloalkenone compounds.

REFERENCE SIGNS LIST

1 Starting material feeding line
2 Vaporizer (equipped with a heater)
3 Catalyst packed reactor (equipped with a heater)
4 Condenser
5 Reaction product receiver

The invention claimed is:
1. A method for producing a 3-methylcycloalkenone compound represented by the following general formula (2), comprising vaporizing a diketone represented by the following general formula (1):

TABLE 2

| | Catalyst comprising zirconium oxide | | | Intramolecular condensation reaction of diketone | | | Mass ratio of diketone relative to catalyst (fold mass) | Reaction product | | |
|---|---|---|---|---|---|---|---|---|---|---|
| | Alumina content (% by mass) | Calcination temperature (° C.) | BET specific surface area (m²/g) | Feed rate of starting material[1] | Condensation temperature (° C.) | Reaction time (hour) | | Conversion (%) | Selectivity (%) | Yield (%) |
| Comparative Example 1 | 0 | — | 63.6 | 0.01 | 340 | 6 | 0.06 | 100 | 0 | 0 |
| Comparative Example 2 | 0 | — | 63.6 | 0.01 | 340 | 12 | 0.12 | 100 | 0 | 0 |

[1]Feed rate (g) of the starting material per hour relative to 1 g of the catalyst (unit: g/g-cat · hr)

As described in Patent Literature 3, even in the case of using zirconium oxide as a catalyst, any desired 3-methylcyclopentadecenone compound was not obtained at all when the feed rate of the starting material was low and the reaction time was not sufficient.

[Example 17] Method for Producing Muscone

The reaction product solution obtained in Example 16 was concentrated and 1200 g of heptane was added thereto, followed by warming to 50° C. The mixture was then cooled slowly to precipitate 2,15-hexadecanedione remaining unreacted. After cooling to −10° C., the precipitated crystal was removed by filtration separation to obtain 1690 g of a heptane solution containing a 3-methylcyclopentadecenone compound. The heptane solution contained 614 g of the

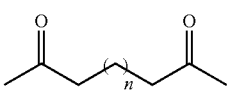
(1)

wherein in formula (1), n represents 8, 9, 10, 11 or 12, and contacting the vaporized diketone of formula (1) with a catalyst consisting of zirconium oxide and an optional additional metal oxide, wherein an amount of the optional additional metal oxide in the catalyst is 3 mass % or less, to cause a vapor-phase intramolecular condensation reaction thereby producing a 3-methylcycloalkenone compound represented by the following general formula (2):

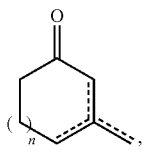

(2)

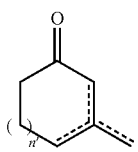

(2')

wherein in formula (2), among the three double lines each consisting of solid and dotted lines, one represents a double bond and the other two represent single bonds, in which the configuration of the double bond may be either cis or trans, and n is as defined in general formula (1), wherein a mass ratio of the vaporized diketone of formula (1) to the catalyst is 0.2 or more.

2. The method according to claim 1, wherein the catalyst consists of zirconium oxide.

3. The method according to claim 1, wherein the catalyst consists of zirconium oxide and an additional metal oxide, wherein an amount of the additional metal oxide in the catalyst is 3 mass % or less.

4. The method according to claim 3, wherein the additional metal oxide is alumina.

5. The method according to claim 1, wherein the diketone represented by general formula (1) is 2,15-hexadecanedione, and the 3-methylcycloalkenone compound represented by general formula (2) generated upon the intramolecular condensation reaction is a 3-methylcyclopentadecenone compound.

6. The method according to claim 1, wherein the catalyst is filled into a reactor, and wherein the method comprises continuously feeding the vaporized diketone represented by general formula (1) to the reactor in an amount of 0.01 to 50 g/hr relative to 1 g of the catalyst filled into the reactor to effect the intramolecular condensation reaction.

7. A method for producing muscone, comprising vaporizing 2,15-hexadecanedione; and contacting the vaporized 2,15-hexadecanedione with a catalyst consisting of zirconium oxide and an optional additional metal oxide, wherein an amount of the optional additional metal oxide in the catalyst is 3 mass % or less, to cause a vapor-phase intramolecular condensation reaction thereby producing a 3-methylcyclopentadecenone compound represented by the following general formula (2'):

wherein among the three double lines each consisting of solid and dotted lines, one represents a double bond and the other two represent single bonds, the configuration of the double bond may be either cis or trans, and n' represents 10, wherein a mass ratio of the vaporized diketone of formula (1) to the catalyst is 0.2 or more, and hydrogenating the produced 3-methylcyclopentadecenone compound.

8. The method for producing muscone according to claim 7, filling wherein the catalyst is filled into a reactor, and wherein the method comprises continuously feeding 2,15-hexadecanedione to the reactor in an amount of 0.01 to 50 g/hr relative to 1 g of the catalyst filled into the reactor to effect the intramolecular condensation reaction.

9. The method for producing muscone according to claim 7, wherein the catalyst consists of zirconium oxide.

10. The method for producing muscone according to claim 7, wherein the catalyst consists of zirconium oxide and an additional metal oxide, wherein an amount of the additional metal oxide in the catalyst is 3 mass % or less.

11. The method for producing muscone according to claim 10, wherein the additional metal oxide is alumina.

12. The method of claim 1, wherein the catalyst is in a molded form.

13. The method of claim 12, wherein the catalyst is in a form of a pellet.

14. The method of claim 13, wherein the pellet has a size of 1 to 10 mm.

15. The method of claim 6, wherein the vaporized diketone is fed into the reactor with a carrier gas.

16. The method of claim 1, wherein the vapor-phase intramolecular condensation reaction is performed at atmospheric pressure.

17. The method of claim 1, wherein the diketone is vaporized in a pristine form.

18. The method of claim 1, wherein the diketone is vaporized in a solution comprising the diketone and a solvent, which is a hydrocarbon.

19. The method of claim 1, wherein the zirconium oxide is uncalcinated zirconium oxide.

20. The method of claim 1, wherein the zirconium oxide is calcinated zirconium oxide.

* * * * *